US008771314B2

(12) United States Patent
Crombie et al.

(10) Patent No.: US 8,771,314 B2
(45) Date of Patent: Jul. 8, 2014

(54) SURGICAL ANCHOR DEVICE (75) Inventors: John Crombie, East Hanover, NJ (US);
Jessica Liberatore, Marlboro, NJ (US);
Robert Nering, Stockton, NJ (US);
Gabriel Jacinto, Princeton, NJ (US);
Simon Cohn, Rutherford, NJ (US)

(73) Assignee: Ethicon, Inc., New Brunswick, NJ (US)

( * ) Notice: Subject to any disclaimer, the term of this patent is extended or adjusted under 35 U.S.C. 154(b) by 1758 days.

(21) Appl. No.: 11/864,722

(22) Filed: Sep. 28, 2007

(65) Prior Publication Data

US 2009/0088797 A1    Apr. 2, 2009

(51) Int. Cl.
*A61B 17/04*    (2006.01)

(52) U.S. Cl.
USPC .......................................................... 606/232

(58) Field of Classification Search
USPC .......................................................... 606/232
See application file for complete search history.

(56) References Cited

U.S. PATENT DOCUMENTS

| 3,752,516 | A | * | 8/1973 | Mumma .......................... 289/17 |
| 4,210,148 | A | | 7/1980 | Stivala |
| 4,235,238 | A | | 11/1980 | Ogiu |
| 4,696,300 | A | | 9/1987 | Anderson |
| 4,705,040 | A | * | 11/1987 | Mueller et al. ................. 606/108 |
| 4,741,330 | A | | 5/1988 | Hayhurst |
| 4,898,156 | A | | 2/1990 | Gatturna et al. |
| 4,946,468 | A | * | 8/1990 | Li ..................................... 606/232 |
| 5,037,422 | A | | 8/1991 | Hayhurst et al. |
| 5,041,129 | A | * | 8/1991 | Hayhurst et al. ............... 606/232 |
| 5,067,956 | A | | 11/1991 | Buford et al. |
| 5,074,874 | A | | 12/1991 | Yoon et al. |
| 5,080,663 | A | | 1/1992 | Mills et al. |
| D331,626 | S | | 12/1992 | Hayhurst et al. |
| 5,203,787 | A | | 4/1993 | Noblitt |
| 5,222,976 | A | | 6/1993 | Yoon |
| 5,224,946 | A | | 7/1993 | Hayhurst et al. |
| 5,236,445 | A | | 8/1993 | Hayhurst et al. |
| 5,269,809 | A | * | 12/1993 | Hayhurst et al. ............... 606/232 |
| 5,312,438 | A | * | 5/1994 | Johnson ........................ 606/232 |
| 5,333,624 | A | | 8/1994 | Tovey |
| 5,358,511 | A | | 10/1994 | Gatturna et al. |
| 5,370,661 | A | | 12/1994 | Branch |
| 5,380,334 | A | | 1/1995 | Torrie et al. |
| 5,403,348 | A | | 4/1995 | Bonutti |
| 5,417,691 | A | | 5/1995 | Hayhurst |
| 5,437,680 | A | | 8/1995 | Yoon |
| 5,456,685 | A | | 10/1995 | Huebner |
| 5,464,426 | A | | 11/1995 | Bonutti |
| 5,486,197 | A | | 1/1996 | Le et al. |

(Continued)

FOREIGN PATENT DOCUMENTS

DE    1001/9922 B4    5/2005
WO    87/01270 A1    3/1987

(Continued)

*Primary Examiner* — Dianne Dornbusch
(74) *Attorney, Agent, or Firm* — Scully Scott Murphy & Presser, P.C.

(57) ABSTRACT

A tissue anchor comprising a body having a longitudinal axis, a proximal end with one set of dimensions and a projected surface area, a distal end with a second set of dimensions and a projected surface area where the respective dimensions of the first and second ends are not identical and the projected areas are substantially the same. The tissue anchor may further have a fixing member to attach the anchor and one or more tissues together or to attach the other structures to tissue.

15 Claims, 10 Drawing Sheets

(56) References Cited

U.S. PATENT DOCUMENTS

| | | | |
|---|---|---|---|
| 5,496,348 A | 3/1996 | Bonutti | |
| 5,507,754 A | 4/1996 | Green et al. | |
| 5,522,846 A | 6/1996 | Bonutti | |
| 5,527,343 A | 6/1996 | Bonutti | |
| 5,534,012 A | 7/1996 | Bonutti | |
| 5,549,630 A | 8/1996 | Bonutti | |
| 5,549,631 A | 8/1996 | Bonutti | |
| 5,569,305 A | 10/1996 | Bonutti | |
| 5,584,836 A | 12/1996 | Ballintyn et al. | |
| 5,584,862 A | 12/1996 | Bonutti | |
| 5,593,425 A | 1/1997 | Bonutti et al. | |
| 5,601,557 A | 2/1997 | Hayhurst | |
| 5,601,558 A | 2/1997 | Torrie et al. | |
| 5,626,614 A * | 5/1997 | Hart | 606/232 |
| 5,643,295 A | 7/1997 | Yoon | |
| 5,647,874 A | 7/1997 | Hayhurst | |
| 5,667,513 A | 9/1997 | Torrie et al. | |
| 5,683,417 A | 11/1997 | Cooper | |
| 5,683,418 A | 11/1997 | Luscombe et al. | |
| 5,690,676 A | 11/1997 | DiPoto et al. | |
| 5,693,060 A | 12/1997 | Martin | |
| 5,713,921 A | 2/1998 | Bonutti | |
| 5,718,717 A | 2/1998 | Bonutti | |
| 5,733,306 A | 3/1998 | Bonutti | |
| 5,735,875 A | 4/1998 | Bonutti et al. | |
| 5,769,894 A | 6/1998 | Ferragamo | |
| 5,782,862 A | 7/1998 | Bonutti | |
| 5,810,848 A * | 9/1998 | Hayhurst | 606/144 |
| 5,814,070 A | 9/1998 | Borzone et al. | |
| 5,814,072 A * | 9/1998 | Bonutti | 606/232 |
| 5,814,073 A | 9/1998 | Bonutti | |
| 5,845,645 A * | 12/1998 | Bonutti | 128/898 |
| 5,873,891 A * | 2/1999 | Sohn | 606/219 |
| 5,891,168 A | 4/1999 | Thal | |
| 5,897,574 A | 4/1999 | Bonutti | |
| 5,921,986 A | 7/1999 | Bonutti | |
| 5,941,899 A * | 8/1999 | Granger et al. | 606/222 |
| 5,941,900 A | 8/1999 | Bonutti | |
| 5,948,002 A | 9/1999 | Bonutti | |
| 5,954,747 A | 9/1999 | Clark | |
| 5,957,953 A | 9/1999 | DiPoto et al. | |
| 5,961,521 A | 10/1999 | Roger et al. | |
| 5,961,538 A | 10/1999 | Pedlick et al. | |
| 5,980,559 A | 11/1999 | Bonutti | |
| 5,989,282 A | 11/1999 | Bonutti | |
| 6,007,567 A | 12/1999 | Bonutti | |
| 6,010,525 A | 1/2000 | Bonutti et al. | |
| 6,033,430 A | 3/2000 | Bonutti | |
| 6,056,752 A | 5/2000 | Roger | |
| 6,056,772 A | 5/2000 | Bonutti | |
| 6,056,773 A * | 5/2000 | Bonutti | 606/232 |
| 6,066,146 A * | 5/2000 | Carroll et al. | 606/148 |
| 6,068,648 A * | 5/2000 | Cole et al. | 606/232 |
| 6,077,292 A | 6/2000 | Bonutti | |
| 6,086,591 A | 7/2000 | Bojarski | |
| 6,099,530 A | 8/2000 | Simonian et al. | |
| 6,102,934 A | 8/2000 | Li | |
| 6,117,160 A | 9/2000 | Bonutti | |
| 6,139,565 A | 10/2000 | Stone et al. | |
| RE36,974 E | 11/2000 | Bonutti | |
| 6,146,406 A | 11/2000 | Shluzas et al. | |
| 6,152,949 A | 11/2000 | Bonutti | |
| 6,159,234 A | 12/2000 | Bonutti et al. | |
| 6,203,565 B1 | 3/2001 | Bonutti et al. | |
| 6,231,606 B1 | 5/2001 | Graf et al. | |
| 6,270,518 B1 | 8/2001 | Pedlick et al. | |
| 6,287,325 B1 | 9/2001 | Bonutti | |
| 6,306,158 B1 | 10/2001 | Bartlett | |
| 6,309,405 B1 | 10/2001 | Bonutti | |
| 6,312,448 B1 | 11/2001 | Bonutti | |
| 6,336,940 B1 | 1/2002 | Graf et al. | |
| 6,364,897 B1 | 4/2002 | Bonutti | |
| 6,397,640 B1 * | 6/2002 | Williams | 66/117 |
| 6,428,562 B2 | 8/2002 | Bonutti | |
| 6,436,124 B1 | 8/2002 | Anderson et al. | |
| 6,464,713 B2 | 10/2002 | Bonutti | |
| 6,500,184 B1 | 12/2002 | Chan et al. | |
| 6,500,195 B2 * | 12/2002 | Bonutti | 606/232 |
| 6,503,267 B2 | 1/2003 | Bonutti et al. | |
| 6,511,498 B1 * | 1/2003 | Fumex | 606/232 |
| 6,533,802 B2 | 3/2003 | Bojarski et al. | |
| 6,554,852 B1 | 4/2003 | Oberlander | |
| 6,572,635 B1 | 6/2003 | Bonutti | |
| 6,592,609 B1 | 7/2003 | Bonutti et al. | |
| 6,599,289 B1 | 7/2003 | Bojarski et al. | |
| 6,623,492 B1 | 9/2003 | Berube et al. | |
| 6,626,917 B1 | 9/2003 | Craig | |
| 6,635,073 B2 | 10/2003 | Bonutti et al. | |
| 6,638,279 B2 | 10/2003 | Bonutti | |
| 6,645,227 B2 | 11/2003 | Fallin et al. | |
| 6,648,892 B2 | 11/2003 | Martello | |
| 6,656,182 B1 | 12/2003 | Hayhurst | |
| 6,656,183 B2 | 12/2003 | Colleran et al. | |
| 6,660,022 B1 | 12/2003 | Li et al. | |
| 6,682,549 B2 | 1/2004 | Bartlett | |
| 6,719,765 B2 | 4/2004 | Bonutti | |
| 6,726,707 B2 | 4/2004 | Pedlick et al. | |
| 6,736,829 B1 | 5/2004 | Li et al. | |
| 6,770,076 B2 * | 8/2004 | Foerster | 606/326 |
| 6,773,450 B2 | 8/2004 | Leung et al. | |
| 6,786,915 B2 * | 9/2004 | Akerfeldt et al. | 606/232 |
| 6,899,722 B2 | 5/2005 | Bonutti | |
| 6,908,466 B1 | 6/2005 | Bonutti et al. | |
| 6,932,834 B2 | 8/2005 | Lizardi et al. | |
| 6,955,683 B2 | 10/2005 | Bonutti | |
| 6,986,781 B2 | 1/2006 | Smith | |
| 7,004,959 B2 | 2/2006 | Bonutti | |
| 7,081,126 B2 | 7/2006 | McDevitt et al. | |
| 7,083,638 B2 * | 8/2006 | Foerster | 606/232 |
| 7,087,073 B2 | 8/2006 | Bonutti | |
| 7,097,654 B1 | 8/2006 | Freedland | |
| 7,104,999 B2 | 9/2006 | Overaker | |
| 7,128,753 B1 | 10/2006 | Bonutti et al. | |
| 7,153,312 B1 | 12/2006 | Torrie et al. | |
| 7,341,558 B2 * | 3/2008 | de la Torre et al. | 600/204 |
| 7,422,596 B2 * | 9/2008 | Therin et al. | 606/232 |
| 7,632,287 B2 * | 12/2009 | Baker et al. | 606/151 |
| 7,645,286 B2 * | 1/2010 | Catanese et al. | 606/151 |
| 7,658,751 B2 * | 2/2010 | Stone et al. | 606/232 |
| 7,749,250 B2 * | 7/2010 | Stone et al. | 606/232 |
| 7,850,712 B2 * | 12/2010 | Conlon et al. | 606/232 |
| 2001/0002439 A1 | 5/2001 | Bonutti et al. | |
| 2001/0002440 A1 | 5/2001 | Bonutti | |
| 2001/0014814 A1 | 8/2001 | Bonutti et al. | |
| 2001/0041916 A1 | 11/2001 | Bonutti | |
| 2001/0044637 A1 | 11/2001 | Jacobs et al. | |
| 2001/0056287 A1 | 12/2001 | Bonutti | |
| 2002/0019649 A1 | 2/2002 | Sikora et al. | |
| 2002/0029067 A1 | 3/2002 | Bonutti | |
| 2002/0087189 A1 | 7/2002 | Bonutti | |
| 2002/0128684 A1 * | 9/2002 | Foerster | 606/232 |
| 2002/0193830 A1 | 12/2002 | Bonutti | |
| 2003/0105474 A1 | 6/2003 | Bonutti | |
| 2003/0130669 A1 | 7/2003 | Damarati | |
| 2003/0135239 A1 * | 7/2003 | Gabriel et al. | 606/232 |
| 2003/0181800 A1 | 9/2003 | Bonutti | |
| 2003/0195565 A1 | 10/2003 | Bonutti | |
| 2003/0204204 A1 | 10/2003 | Bonutti | |
| 2004/0010287 A1 | 1/2004 | Bonutti | |
| 2004/0098050 A1 | 5/2004 | Foerster et al. | |
| 2004/0111117 A1 | 6/2004 | Colleran et al. | |
| 2004/0167548 A1 | 8/2004 | Bonutti | |
| 2004/0172033 A1 | 9/2004 | Bonutti | |
| 2004/0210241 A1 | 10/2004 | James et al. | |
| 2004/0220591 A1 | 11/2004 | Bonutti | |
| 2004/0249395 A1 | 12/2004 | Mikkaichi et al. | |
| 2004/0260345 A1 * | 12/2004 | Foerster | 606/232 |
| 2005/0015101 A1 | 1/2005 | Gibbens et al. | |
| 2005/0033366 A1 * | 2/2005 | Cole et al. | 606/232 |
| 2005/0059984 A1 | 3/2005 | Chanduszko et al. | |
| 2005/0065409 A1 * | 3/2005 | de la Torre et al. | 600/204 |
| 2005/0113851 A1 * | 5/2005 | Swain et al. | 606/151 |
| 2005/0119670 A1 | 6/2005 | Kerr et al. | |
| 2005/0216040 A1 | 9/2005 | Gertner et al. | |

(56) References Cited

U.S. PATENT DOCUMENTS

| | | |
|---|---|---|
| 2005/0222620 A1 | 10/2005 | Bonutti |
| 2005/0240227 A1 | 10/2005 | Bonutti |
| 2005/0267534 A1 | 12/2005 | Bonutti et al. |
| 2005/0277986 A1* | 12/2005 | Foerster et al. ............... 606/232 |
| 2006/0004409 A1* | 1/2006 | Nobis et al. .................... 606/232 |
| 2006/0015108 A1 | 1/2006 | Bonutti |
| 2006/0030884 A1 | 2/2006 | Yeung et al. |
| 2006/0142799 A1 | 6/2006 | Bonutti |
| 2006/0167495 A1 | 7/2006 | Bonutti et al. |
| 2006/0200199 A1 | 9/2006 | Bonutti et al. |
| 2006/0217765 A1 | 9/2006 | Bonutti et al. |
| 2006/0229623 A1 | 10/2006 | Bonutti et al. |
| 2006/0235470 A1 | 10/2006 | Bonutti et al. |
| 2006/0241695 A1 | 10/2006 | Bonutti et al. |
| 2006/0265009 A1 | 11/2006 | Bonutti et al. |
| 2006/0265011 A1 | 11/2006 | Bonutti |
| 2007/0100351 A1 | 5/2007 | Deffenbaugh |
| 2007/0112383 A1* | 5/2007 | Conlon et al. ................. 606/232 |
| 2007/0112384 A1* | 5/2007 | Conlon et al. ................. 606/232 |
| 2007/0112385 A1* | 5/2007 | Conlon .......................... 606/232 |
| 2007/0142838 A1 | 6/2007 | Jordan |
| 2008/0033232 A1* | 2/2008 | Catanese et al. ................. 600/29 |
| 2008/0033488 A1* | 2/2008 | Catanese et al. .............. 606/232 |
| 2008/0039894 A1* | 2/2008 | Catanese et al. .............. 606/232 |
| 2010/0076462 A1* | 3/2010 | Bakos et al. ................... 606/146 |

FOREIGN PATENT DOCUMENTS

| | | |
|---|---|---|
| WO | 2003/000140 A1 | 1/2003 |
| WO | 2003/003925 A1 | 1/2003 |
| WO | 2004/004727 A1 | 1/2005 |

* cited by examiner

SURGICAL ANCHOR DEVICE

BACKGROUND OF THE INVENTION

1. Field of Invention

The present invention generally relates to surgical implements, and more particularly relates to a self-penetrating tissue anchor, which is capable of creating its own pathway into tissue, reducing trauma caused to the tissue and enhancing its stabilization in the tissue.

2. Description of Related Art

Suture anchors are generally known in the art. U.S. Pat. No. 5,041,129 to Hayhurst describes a suture anchor for securing a suture to body tissue in an arthroscopic surgical procedure. The suture anchor comprises a tubular member with a through hole through which a suture extends. The terminal end of the suture is secured to the leading end of the anchor by forming a knot. A slot is formed on the suture anchor which extends from the trailing end of the suture anchor toward the leading end of the suture anchor. Once the anchor is inserted into tissue, tension is applied to the suture, shifting the orientation of the anchor to a position generally transverse to the free end of the suture. Insertion of the anchor into tissue requires the anchor to be confined within a hollow outer needle of a cannulated insertion tool. The outer dimensions of the insertion tool are greater than those of the anchor. Because of this, the introduction of the anchor into tissue requires a pathway to be created in the tissue larger than the outer dimensions of the anchor.

U.S. Pat. No. 6,500,195 to Bonutti describes a suture anchor having a polygonal cross-section configuration with flat outer side surfaces connected by a plurality of outer corner portions. After initial insertion of the anchor, the anchor is rotated to orientate it parallel to the tissue surface. This orientation provides good fixation within tissue. However, to achieve this orientation, an offset force is required to be applied by a pusher member to the anchor. A tubular guide member is also required to introduce the anchor into tissue. The outer dimensions of the guide member are greater than those of the anchor and, as a result, necessitate a tissue opening that is greater than the dimensions of the anchor.

BRIEF SUMMARY OF THE INVENTION

The present invention provides a tissue anchor adapted for effectively anchoring a body in all types of tissue structures, including but not limited to hard tissue, such as bone, and soft tissue, such as muscle and fascia.

According to one aspect of the present invention, an anchor device is provided. The anchor comprises a body having a longitudinal axis, a proximal end, a distal end, and a longitudinal suture passageway that defines a first suture exit near the distal end and a second suture exit near the proximal end. The body further comprises a bridge that extends between the first suture exit and the second suture exit. The bridge has a center point defined as the point midway between the first suture exit and the second suture exit. The body has a first portion distal of the center point and a second portion proximal of the center point. The length of the first portion and the second portion are not equal, and the projected surface area of the first portion is substantially equal to the projected surface area of the second portion.

According to another aspect of the present invention, an anchor device is provided. The anchor comprises an elongated body extending along a longitudinal axis, an elongated anchor driver engageable with the body and a suture configured to pass through the body. The body comprises a distal end, which has a tapered portion having a tissue penetrating tip, and a proximal end. The body flirter comprises a distal channel extending at least through a portion of the tapered portion and a proximal bore that communicates with the channel. The anchor driver has a distal end configured to releasably engage with the proximal bore. The suture passes through the channel and the bore.

According to yet another aspect of the present invention, an anchor device is provided. The anchor comprises an elongated body extending along a longitudinal axis, an elongated anchor driver engageable with the body and a suture configured to pass through the body. The body comprises a first portion, which has a tapered portion having a tissue penetrating tip. The body further comprises a channel extending at least through a portion of the tapered portion. The body further comprises a second portion extending from the first portion and having a substantially cylindrical configuration, and a bore provided in the second portion and communicating with the channel. The anchor driver has an end configured to releasably engage with the bore. The suture passes through the channel and the bore.

According to still another aspect of the present invention, an anchor device is provided. The anchor comprises a body having a projected surface area having a centroid. The body has a longitudinal axis and a centroid plane that is perpendicular to the longitudinal axis and intersects the centroid. The centroid plane divides the body into a first portion, having a first projected surface area and a first dimension, and a second portion, having a second projected surface area and a second dimension. The first projected surface area and second projected surface area are approximately equal, and the first dimension and the second dimension are unequal.

BRIEF DESCRIPTION OF THE DRAWINGS

The invention will be illustrated in more detail in the following description, with reference made to the accompanying drawings. In the drawings.

DETAILED DESCRIPTION OF THE INVENTION

The present invention now will be described in detail hereinafter with reference to the accompanying drawings, in which preferred embodiments of the invention are shown. However, this invention may be embodied in many different forms and should not be construed as limited to the embodiments set forth herein; rather, these embodiments are provided so that this disclosure will be thorough and complete, and will fully convey the scope of the invention to those skilled in the art. Like numerals refers to like elements throughout.

The term "tissue" used in the description includes but not limited to soft tissue, such as tendons, ligaments, muscle, skin, fat, fascia, organs and hard tissue, such as bone, cartilage and any other tissue suitable for anchoring a body in tissue.

The term "fixing member" is a member that is used to attach the anchor and one or more tissues together or to attach a structure to tissue. For example, the fixing member may be a suture that passes through an anchor or is affixed to an anchor. In one embodiment, the structure is a hernia mesh that may be fixed to an abdominal wall of a patient through a suture fixing member and anchor combination. The fixing member may be an integral part of the anchor or may be a separate element that is movable with respect to the anchor.

Figure 1:
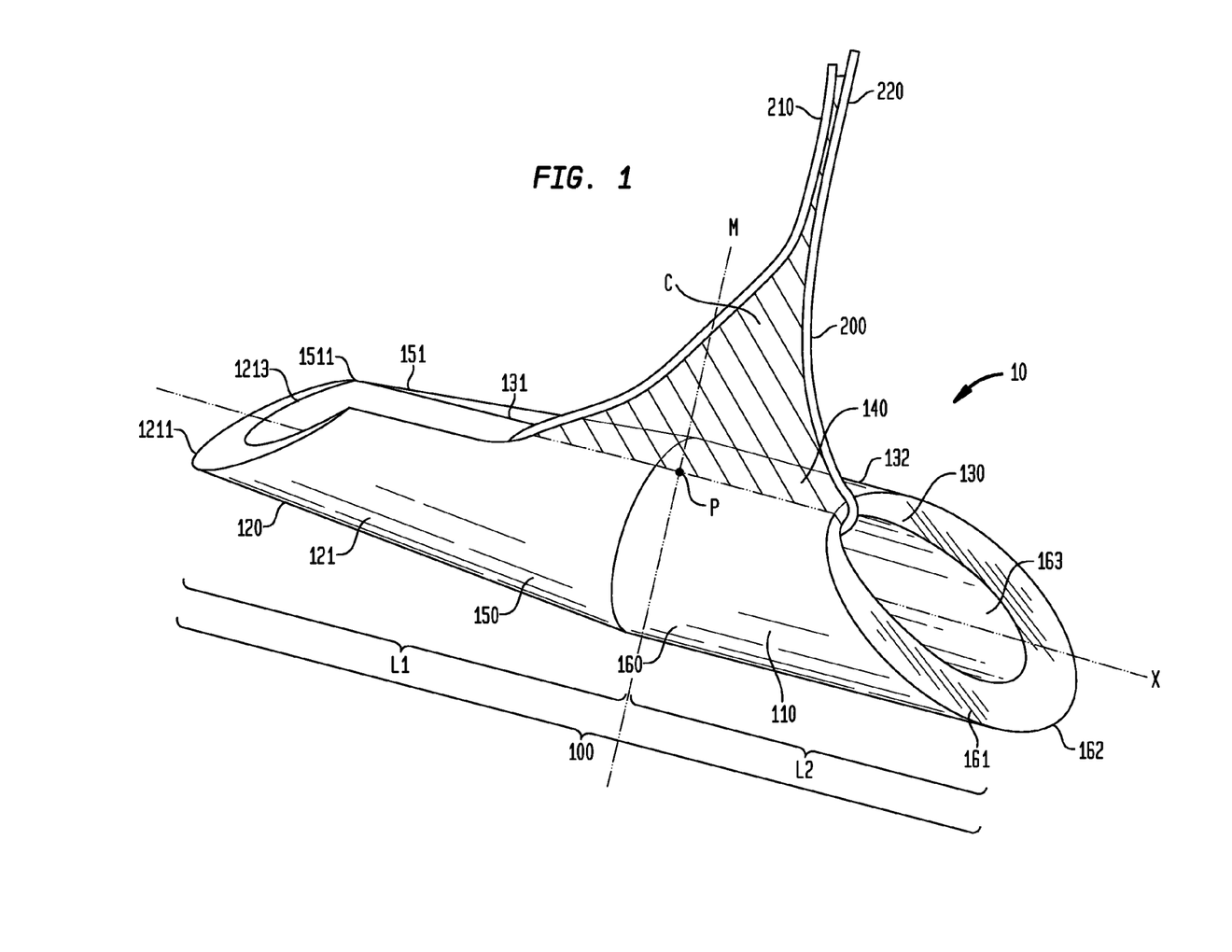
FIG. 1 is a perspective view of the self-penetrating anchor according to the present invention, illustrating the anchor-suture combination.

FIGS. 1-5 illustrate one embodiment of the self-penetrating anchor according to the present invention, indicated generally by the numeral 10. In this embodiment, anchor 10 comprises a substantially elongated body 100 having a longitudinal axis X. As shown in FIG. 1, body 100 comprises a proximal end 110, a distal end 120 and has a longitudinal suture passageway 130. Suture passageway 130 defines a first suture exit 131 near distal end 120 and a second suture exit 132 near proximal end 110. Body 100 further comprises a bridge 140 extending between first suture exit 131 and second suture exit 132. Bridge 140 has a center point P defined as the point midway between first suture exit 131 and second suture exit 132. A central plane M is substantially perpendicular to the longitudinal axis X of body 100 and intersects bridge 140 at the center point P. Body 100 further comprises a first portion 150 and a second portion 160 divided by central plane M, with the first portion being distal to the central plane and the second portion being proximal to the central plane. As shown in FIG. 1, distal end 120 of this embodiment comprises a tapered portion 121 having a distal tip 1211. Tapered portion 121 includes a distal surface 1213 defining a distal plane A (depicted clearly in FIG. 3) inclined toward longitudinal axis X from distal tip 1211. Distal tip 1211 is preferably sharp, such that when a force is applied to the anchor generally along the longitudinal axis X from the proximal end 110, distal tip 1211 pierces tissue. Distal surface 1213 is configured to smoothly transition the initial puncture created by distal tip 1211 to an opening that will accommodate the widest cross section of the anchor.

First portion 150 includes a slot 151 formed along the upper side of the anchor to communicate with suture passageway 130. At least a portion of the slot 151 is dimensioned to accept suture 200 so that the suture can slide along slot 151 from a distal point at a mouth 1511 of the slot to first suture exit 131. The width of slot 151 may be less than the diameter of the suture if it is desired to enable the suture to be held firmly by the anchor. Further, slot 151 could be closed at its end close to distal surface 1213.

Figure 3:
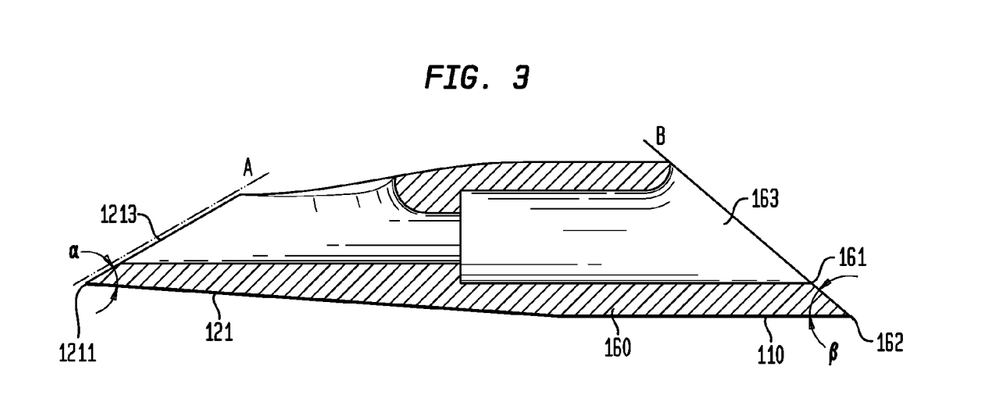
FIG. 3 is a longitudinal cross section view of the self-penetrating anchor according to the present invention.

The self-penetrating functionality of the anchor is achieved by the tapered configuration of the distal end of the anchor. As shown in FIG. 3, distal plane A defined by distal surface 1213 forms an angle α with the lower side of tapered portion 121. A smaller angle α results in a more pointed tip to pierce tissue with less force. Preferably, the angle α is in the range from 20°-45° and more preferably between 25° and 35°. The length of tapered portion 121 is preferably in the range from 50% to 75% of the overall length of the anchor.

Figure 6:
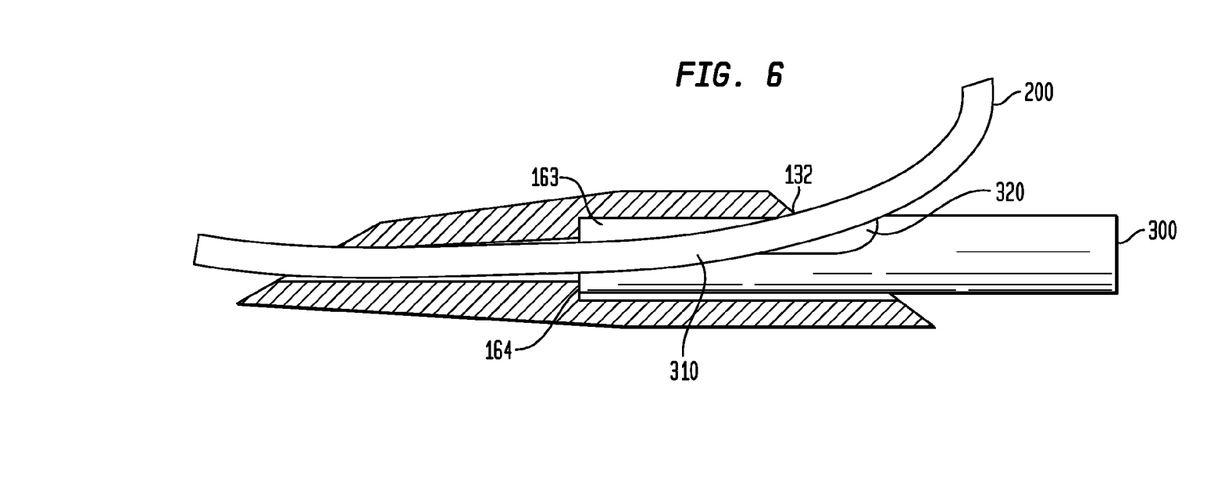
FIG. 6 is a longitudinal cross section view of the self-penetrating anchor and an anchor driver engaging the anchor, illustrating the driver-in-anchor configuration which is capable of providing a suture relief feature.

The second portion 160 serves to fix and hold anchor 10 in the tissue. Referring to FIG. 6, second portion 160 cooperates with an anchor driver 300 for carrying and driving anchor 10 into tissue. The second portion 160 is formed with a proximal surface 161, which forms a proximal plane B (FIG. 3) inclined toward the longitudinal axis X from a proximal tip 162. Preferably, plane A and plane B are inclined toward the longitudinal axis X from opposite directions, so that the two planes intersect each other. As shown in FIG. 3, proximal plane B forms an angle β with the lower side of proximal end 110. Preferably, angle β is in the range from 25°-65°. More preferably, angle β is about 35°.

Referring to FIG. 1, in one embodiment, the length L1 of first portion 150, defined as the length from distal tip 1211 to central plane M, is not equal to the length L2 of second portion 160, defined as the length from proximal tip 162 to central plane M.

Continuing to refer to FIG. 1, suture passageway 130 is sized to at least accommodate a suture 200 having a leading end 210 and a trailing end 220. When the anchor-suture combination is delivered into tissue, leading end 210 extends from anchor body 100 at first suture exit 131 and trailing end 220 extends from anchor body 100 from suture passageway 130. Subsequently, when anchor 10 is rotated by tensioning suture 200 to an orientation substantially perpendicular to the piercing direction of the anchor, leading end 210 extends from anchor body 100 at first suture exit 131 and trailing end 220 extends from anchor body at second suture exit 132, and accordingly suture 200 forms a suture triangle C within the tissue, as shown in FIG. 1. Suture triangle C is substantially symmetrical relative to central plane M.

When the anchor is in its final position, the lower side of suture triangle C is coincident with the top surface of bridge 140, with the midpoint of the lower side of triangle C overlaid on center point P of bridge 140, and the point where leading end 210 and trailing end 220 of the suture become substantially parallel being substantially in line with central plane M.

Figure 4:
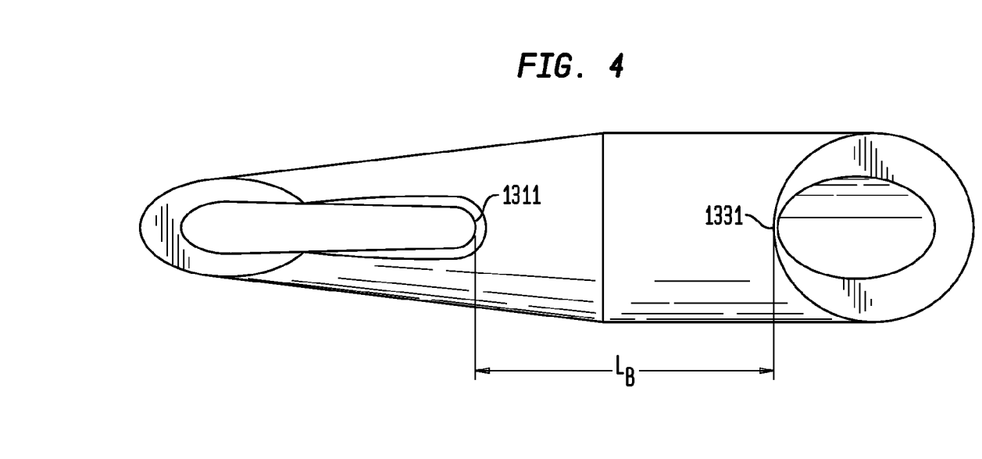
FIG. 4 is a top view of the self-penetrating anchor according to the present invention.

As shown in FIG. 4, the length $L_B$ of bridge 140 determines the area of suture triangle C. Generally, the larger the area of the suture triangle, the more trauma may be caused to the tissue as the suture above anchor 10 displaces tissue that would otherwise reside at a position closer to anchor 10. Thus, it is desirable to minimize the area of suture triangle C. This end can be achieved by the provision of slot 151 in first portion 150 of the anchor. In other words, slot 151 can be lengthened or shortened, thereby shortening or lengthening the length of bridge 140 and decreasing or increasing the area of suture triangle C.

Figure 2:
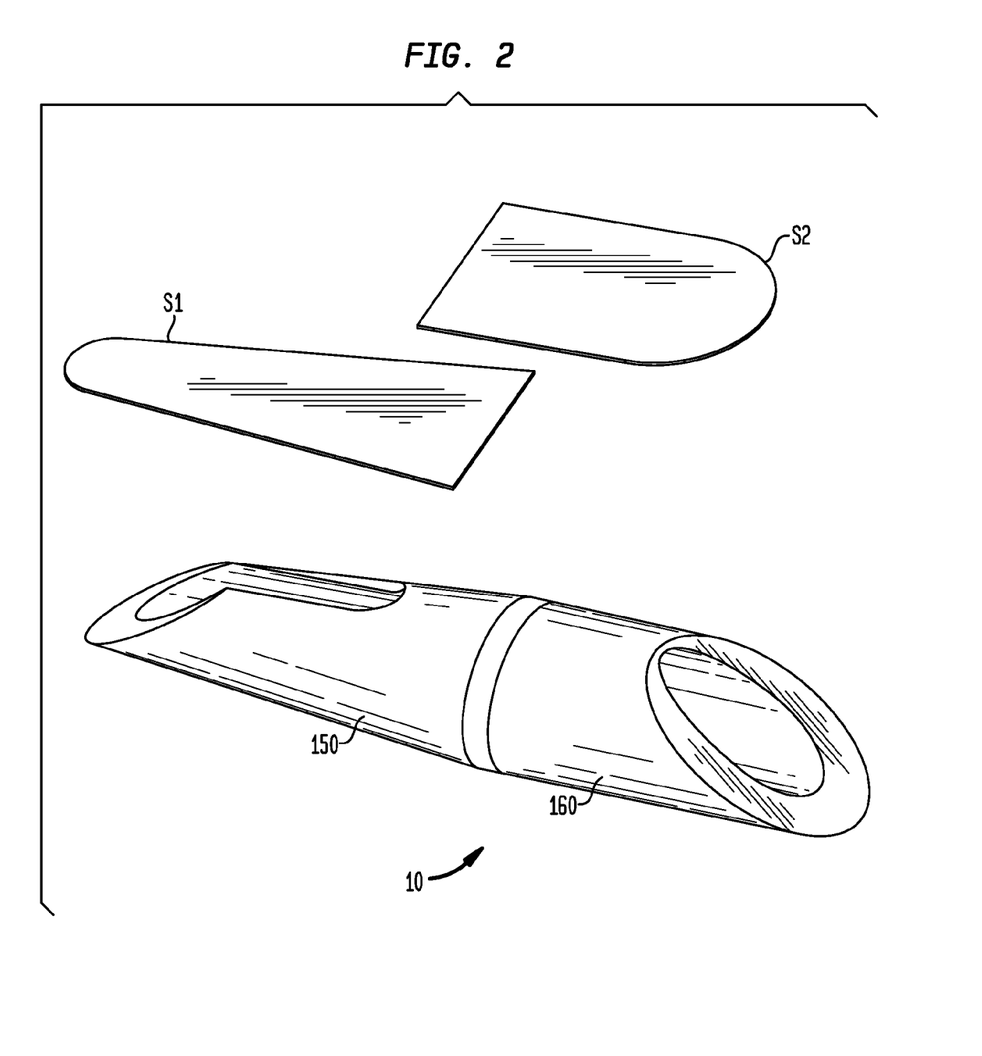
FIG. 2 is another perspective view of the self-penetrating anchor according to the present invention, illustrating the relationship between the projected surface areas of two portions of the anchor.

FIG. 2 illustrates the relationship between the projected surface areas of the first portion 150 and the second portion 160 of the anchor body when anchor 10 is implanted and viewed from above. As shown in FIG. 2 (and more fully described below), the projected surface area S1 of first portion 150 is substantially equal to the projected surface area S2 of the second portion 160. The substantially equal projected areas of first portion 150 and second portion 160 act to make the accidental pulling-out of the anchor more difficult. During operation, anchor 10 is driven into the tissue with a tissue driver and subsequently rotated by tensioning suture 200 so that anchor 10 assumes an orientation that is substantially perpendicular to the piercing direction, to form the suture triangle C with a portion of leading end 210 and a portion of trailing end 220 of the suture assuming a position that is substantially perpendicular to longitudinal axis X of the anchor. When suture 200 is tensioned, a counter force is applied to the projected surface facing the tissue on either side of central plane M. Since the projected surface areas of first portion 150 and second portion 160 are substantially equal, the counter forces applied on the first portion and the second portion are essentially balanced relative to central plane M and center point P. Thus, the anchor retains its orientation in tissue and the pullout force is maximized to render accidental pulling-out of the anchor less likely.

Figure 2A:
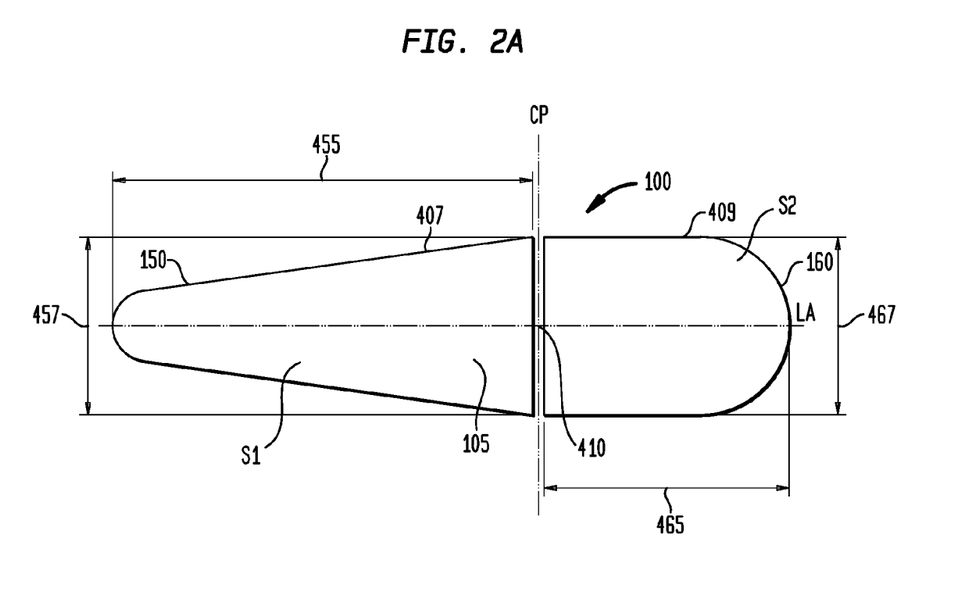
FIG. 2a is a top plan view showing the projected surface area of another embodiment of the self-penetrating anchor according to the present invention.

FIG. 2a depicts the projected surface areas S1 and S2 shown in FIG. 2, again from the vantage point of the surface of the tissue within which the anchor is positioned after rotation. In this view, body 100 of anchor 10 has a projected surface area 105, which is the two-dimensional surface area projected by three-dimensional body 100. Projected surface area 105 has a centroid 410. Body 100 has a longitudinal axis LA and a centroid plane CP, which is a plane substantially perpendicular to the longitudinal axis of body 100 that intersects the centroid 410.

In FIG. 2a, the projected surface areas S1 and S2 are separated by the centroid plane CP, which coincides with the central plane M in this embodiment. However, since the centroid plane CP is defined as the plane intersecting centroid 410 of the entire projected surface area 105 of the anchor body 100 while the central plane M is defined as the plane interesting the midpoint P of the bridge 140 connecting the two opposite suture exits 131 and 132, the centroid plane CP and the central plane M of anchor body 100 do not necessarily coincide with each other.

Body 100 is also divided by centroid plane CP into first portion 150 and second portion 160. Accordingly, the projected surface area 105 is divided into a first projected surface area 407 and a second projected surface area 409 by the centroid plane CP. First projected surface area 407 is the two-dimensional surface area projected by three-dimensional first portion 150 and second projected surface area 409 is the two-dimensional surface area projected by three-dimensional second portion 160. First projected surface area 407 is substantially equal to second projected surface area 409. First portion 150 has a first length 455 and a first width 457. Second portion 160 has a second length 465 and a second width 467. Though first portion 150 and second portion 160 are shown in FIG. 1 as having an oval cross section, in fact, first body portion 150 and second body portion 160 may have any type of cross section. For example, first portion 150 or second portion 160 may have a circular, or polygonal cross-section, including a triangular or square cross-section. In addition, the cross-sectional shapes of the first portion or the second portion need not be constant. The cross-section may taper, as is shown in FIGS. 1 and 3 by numeral 121. It may also taper both inwardly and outwardly so as to project a concave profile. As a result, first width 457 is defined as the maximum width of the first projected surface area 407 of first body portion 150, regardless of what type of cross-section the first portion 150 has. Similarly, second width 467 is defined as the maximum width of the second projected surface area 409 of second portion 160, regardless of what type of cross-sectional shape second body portion 160 has. First length 455 is defined as the length from the centroid plane CP to the outmost point of first portion 150 along the longitudinal axis LA and second length 465 is defined as the length from the centroid plane CP to the outmost point of second portion 160 along the longitudinal axis LA.

Depending on the particular embodiment, first portion 150 may have a first dimension, such as a first length 455 and/or a first width 457, that differs from or is not equal to the respective second dimensions of the corresponding dimensions of the second portion 160. In the embodiment depicted in FIG. 2a, both the first length 455 and first width 457 are not equal to the second length 465 and the second width 467. In other embodiments, one of these dimensions (length or width) could be substantially equal, but the other dimension would not be equal. However, it is important that the projected surface areas 407 and 409 are substantially equal to each other. The substantially equal projected surface areas 407 and 409 result in relatively balanced forces on either side of anchor body 100 when the anchor is disposed within the tissue and a tensioning force is applied thereto along a point substantially aligned with the centroid plane. This serves to orient and maintain the anchor body 100 at a position substantially perpendicular to the piercing direction into the tissue surface (refer to FIGS. 12a-12c) and maximizes the resistive force required to remove the anchor from the tissue, and conversely maximizes the holding capability of the anchor.

Figure 5:
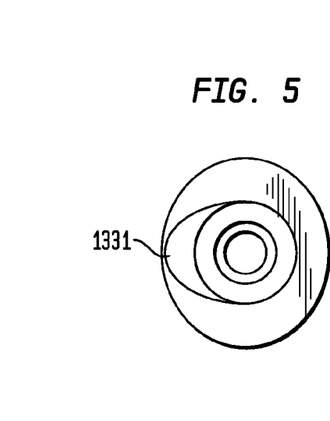
FIG. 5 is a side view of the self-penetrating anchor according to the present invention.

In addition, as shown in FIGS. 4 and 5, anchor body 100 may have a first curved portion 1311 formed at first suture exit 131 and a second curved portion 1331 formed at second suture exit 132. The curved portions provide a smooth contact surface for suture 200 when the suture is tensioned, to protect the suture from being abraded.

Figure 9:
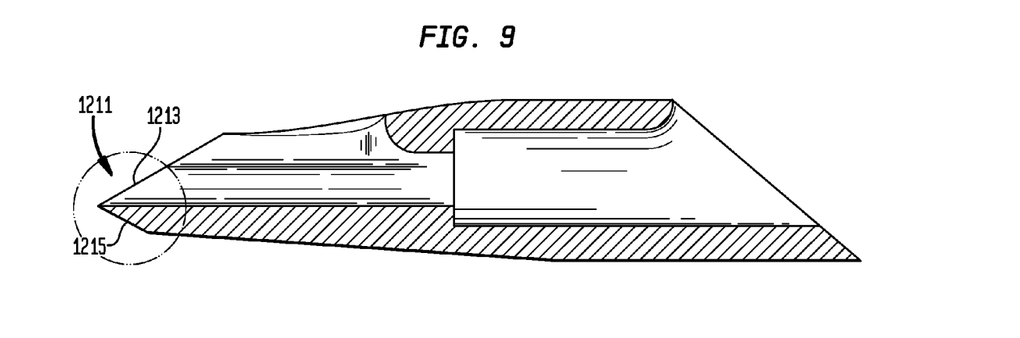
FIG. 9 is a longitudinal cross section view of another variation of the self-penetrating anchor according to the present invention.
Figure 10:
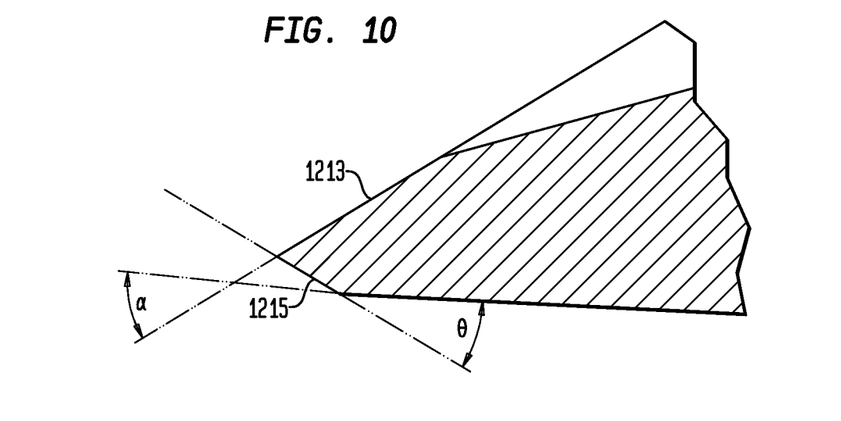
FIG. 10 is an enlarged cross section view of the circled portion of FIG. 9.

FIGS. 9 and 10 illustrate another embodiment of the tapered portion having an alternate tissue penetrating distal tip 1211. When the distal tip pierces tissue, it is possible that the tip may be deformed or curled, especially when the anchor is made of plastic or polymer, the angle α is relatively small, and/or the tissue is non-elastic or hard. Accordingly, the embodiment depicted in FIGS. 9 and 10 is designed to provide increased resistance to tip deformation. In this embodiment, a piece of the tapered portion at its tip is removed to provide a bi-angle structure for the distal penetrating tip; i.e., the tapered portion is provided with a second distal surface 1215, which intersects distal surface 1213 and forms an angle θ with the lower side of the tapered portion. This bi-angle structure increases the ability of the tip to resist deformation or curling when penetrating tissue.

As shown in FIG. 3, the second portion 160 has a proximal bore 163 formed in the proximal end of anchor 10. Proximal bore 163 is sized and configured to accept an anchor delivery device, such as an anchor driver 300 shown in FIG. 6. Anchor driver 300 provides a driving force to drive the anchor into tissue. Proximal bore 163 communicates or forms part of suture passageway 130 of anchor 10. Although in this embodiment, proximal bore 163 is shown as being entirely contained within second portion 160 of the anchor, the bore may extend into first portion 150, as bore 163 primarily is designed to provide a structure to releasably engage with anchor driver 300.

Referring to FIG. 6, anchor driver 300 has a distal end 310 which is configured to releasably engage with proximal bore 163 to drive the anchor into tissue. In this embodiment, proximal bore 163 has a dimension larger than the distal portion of suture passageway 130 to form a shoulder 164 at the interface between proximal bore 163 and the intersection of suture passageway 130. Driver distal end 310 at least partially abuts shoulder 164 to provide a driving force to anchor body 100. However, the releasable engagement of anchor driver 300 and anchor body 100 can be implemented by other configurations. For example, screw threads may be formed respectively on the outer side of distal end of the anchor driver and the inner side of the second portion of the anchor so that the driver and anchor could be releasably engaged through relative rotational movement between the driver and anchor.

In addition, the second portion 160 of the body and the elongate anchor driver 300 are configured such that, when the distal end 310 of the anchor driver 300 is engaged with the proximal bore 163 of the anchor body, a suture relief feature is provided to allow the suture to reside and move in the suture relief feature without being pinched between the anchor body 100 and the anchor driver 300.

Figure 7:
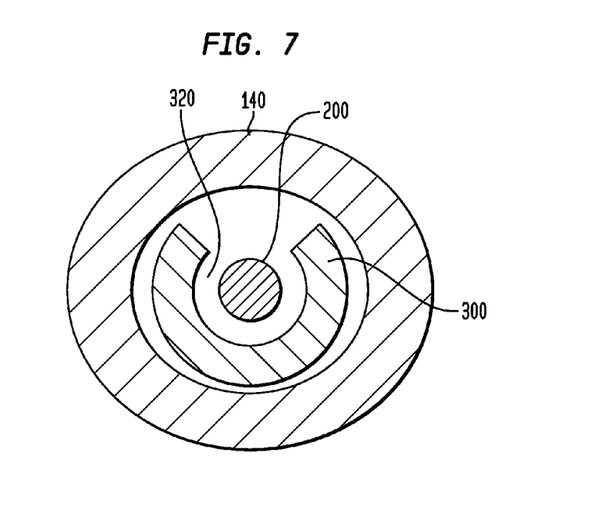
FIG. 7 is a cross section view of a distal end of the anchor driver, illustrating a recess formed in the driver to implement the suture relief feature.
Figure 11:
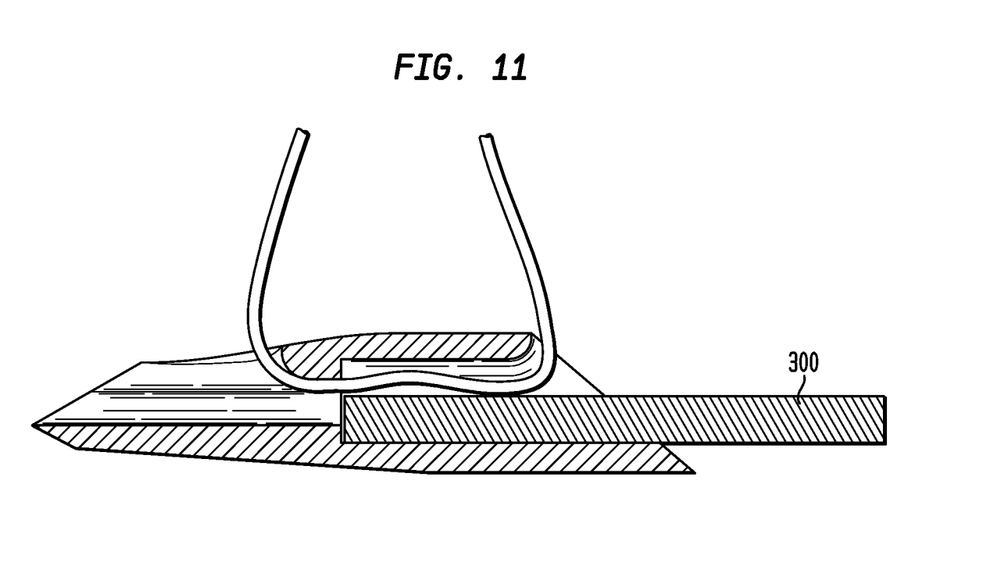
FIG. 11 is a longitudinal cross section view of an embodiment delivery device and suture anchor that provides a suture relief feature.

FIGS. 6 and 7 illustrate one embodiment of the anchor driver, which, in combination with second portion 160 of anchor body 100, provides the suture relief feature stated above. In this embodiment, anchor driver 300 has a recess 320 extending proximally from distal end 310 of anchor driver 300 to a position of anchor driver 300 beyond second suture exit 132, such that suture 200 can pass through the space between suture exit 132 and recess 320, without being pinched at second suture exit 132. Further, recess 320 is formed to communicate with suture passageway 130 to allow suture 200 to enter recess 320 from suture passageway 130 without being pinched at shoulder 164. For example, recess 320 could be a U-shaped channel as shown in FIG. 7. The channel is formed to have enough depth and length, to allow suture 200 reside and move in the space defined by recess 320 and proximal bore 163, when anchor driver 300 engages second portion 160 of the anchor. Anchor driver 300 and second portion 160 may have other mating configurations, in addition to the above described, that could provide the suture relief feature. For example, FIG. 11 shows an alternate embodiment where the relief is provided by altering the configuration of proximal bore 163. In FIG. 11, anchor driver 300 is designed to fit into proximal bore 163 and suture passageway 130 runs along the top portion of proximal bore 163. Anchor driver 300 and proximal bore 163 may be designed so that the anchor driver 300 has mating features with proximal bore 163 so that it can only reside within the lower section of proximal bore 163. For example, anchor driver 300 may have a trapezoidal cross section that mates with a proximal bore cross-section that matches at least a portion of the outer surface of anchor driver 300.

Figure 8:
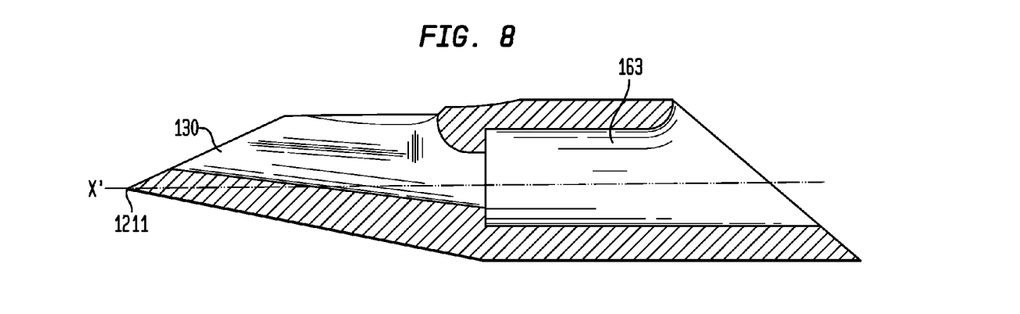
FIG. 8 is a longitudinal cross section view of a variation of the self-penetrating anchor according to the present invention.

Preferably, the proximal bore is configured to be geometrically symmetrical along a center axis of the bore. For example, as shown in FIG. 8, proximal bore 163 has a substantially oval cross section having a center axis X'. Proximal bore 163 may have other suitable cross-sections, for example, round or polygonal. As is shown in FIG. 1, proximal bore 163 can be configured to be concentric with the distal portion of suture passageway 130. However, bore 163 may not be aligned with the distal portion of suture passageway 130, as shown in FIG. 8, in which a portion of suture passageway 130 is inclined relative to proximal bore 163. In this embodiment, it is preferred that distal tip 1211 of first body portion 150 is configured to be aligned with the center axis X', to allow the anchor driver to directly transfer the force to the distal tip 1211 for piercing tissue.

Figure 12A:
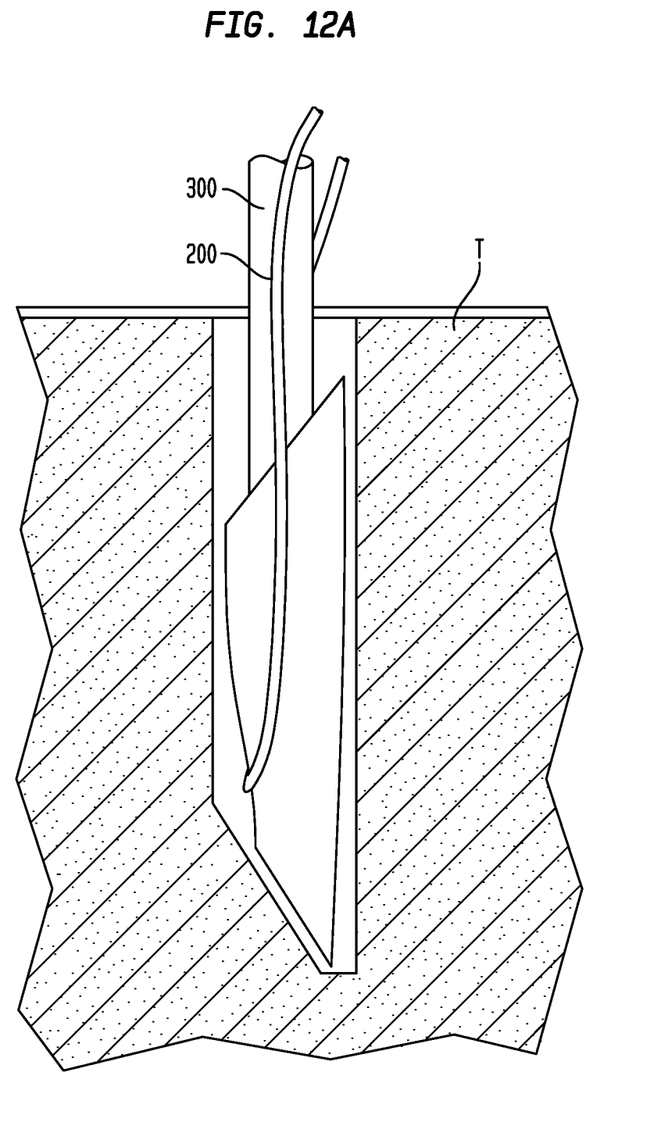
FIGS. 12a-12c are plan views showing the rotation and fixation of the anchor when it is delivered into tissue.
Figure 12B:
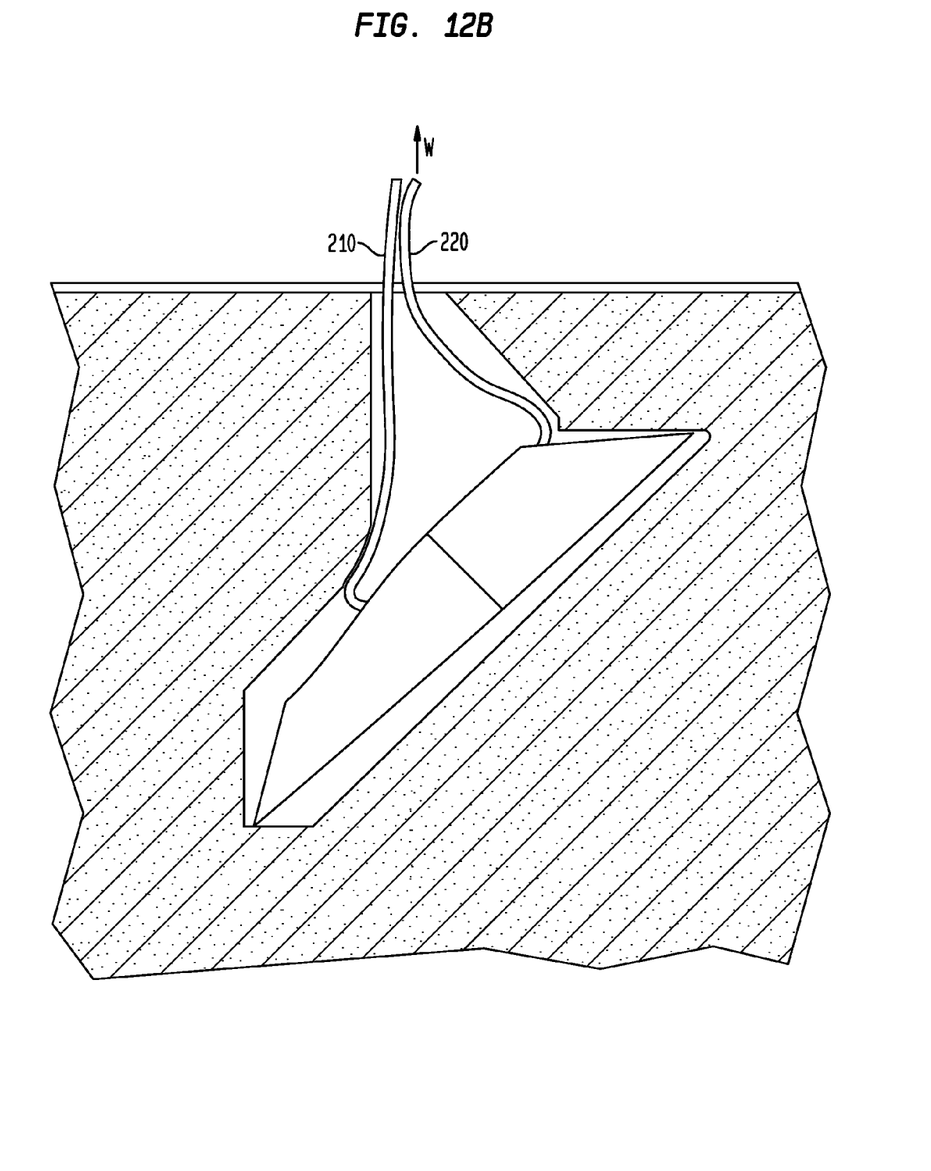
Figure 12C:
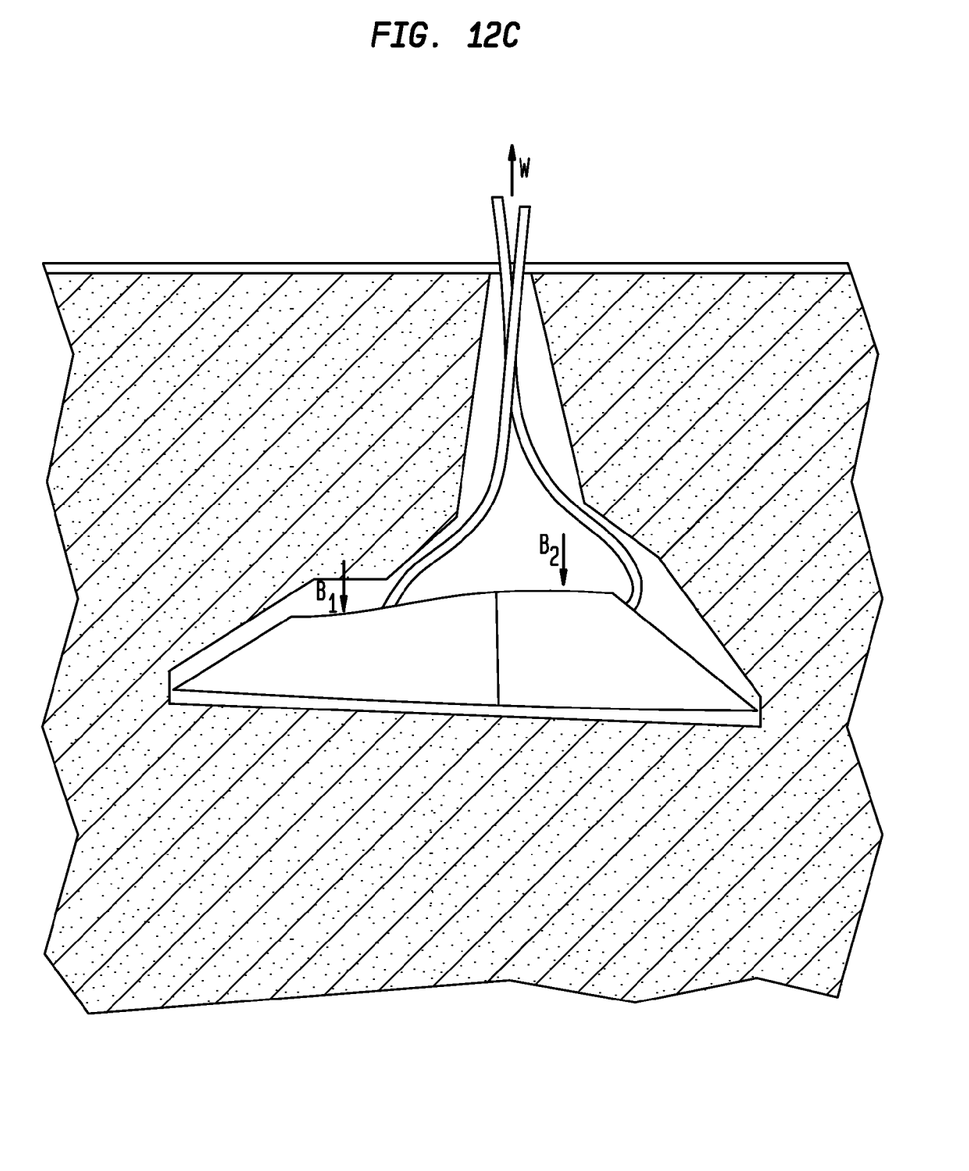

FIGS. 12a-12c are plan views showing the rotation and fixation of the anchor when it is delivered into tissue. As shown in FIG. 12a, the self-penetrating anchor pierces tissue T under the force of anchor driver 300. As shown in FIG. 12b, after the anchor is advanced to a desired location in the tissue, anchor driver 300 having been withdrawn, suture leading and trailing ends 210, 220 are tensioned (as indicated by arrow W) to rotate the anchor. As shown in FIG. 12c, under the tensioning force, the anchor is rotated to an orientation that is substantially perpendicular to the piercing direction of the anchor, and the anchor is firmly fixed in this position by the balanced forces $B_1$ applied on first body portion 150 and $B_2$ applied on second body portion 160 at either side of central plane M.

Figure 13:
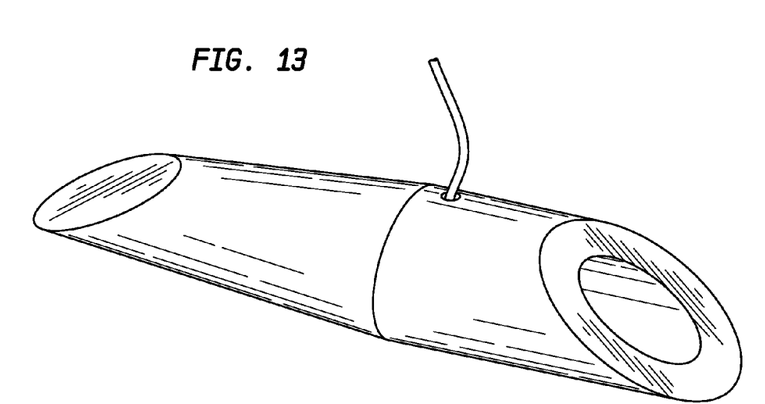
FIG. 13 is a perspective view showing another embodiment of the anchor where the suture is attached to the anchor rather than passes though suture passageway.

FIG. 13 shows an embodiment of the anchor where the suture is attached to the anchor rather than passes through a suture passageway. The suture is fixedly attached at a location substantially aligned with the central plane CP and along the top surface of the anchor. The suture may be attached by any number of ways including, but not limited to, insert molding, gluing, or tying. Filament in other forms than suture can be attached to the anchor depending on the circumstances of surgery.

Figure 14:
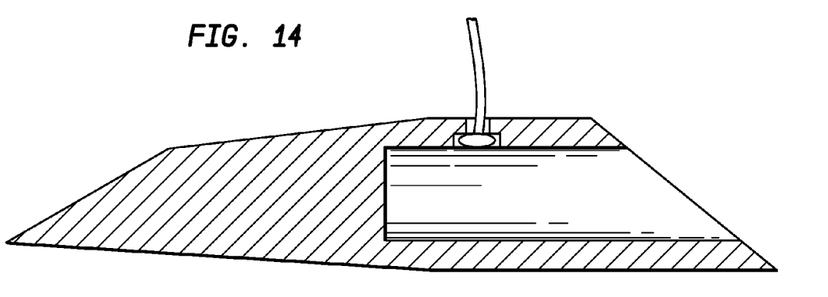
FIG. 14 is a cross-sectional view of the anchor in FIG. 13, showing the way the suture is fixedly attached to the anchor.

FIG. 14 is a cross-sectional view of the anchor in FIG. 13, showing the way the suture is attached to the anchor. The suture is held in place by having an enlarged section, for example, a knot, that fits within an enlarged section of a through hole, the through hole extending from the upper surface of the anchor into the proximal bore 163.

Figure 15:
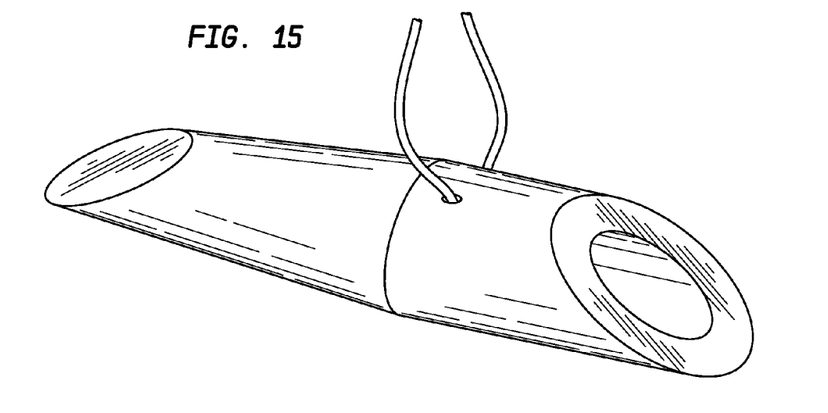
FIG. 15 is a perspective view showing yet another embodiment of the anchor where the suture is attached to the anchor rather than passes though suture passageway.

FIG. 15 shows yet another an embodiment of the anchor where the suture is attached to the anchor rather than passes through a suture passageway. The suture is slidably attached to the upper portion of the anchor at a location substantially aligned with the central plane CP of the anchor. The suture passes through a hole formed within the anchor body in a direction perpendicular to the longitudinal axis of proximal bore 163. However, the hole for the filament may be oriented in any direction relative to the longitudinal axis 'X' of the anchor.

The present invention may be embodied in other specific forms without departing from its spirit or essential characteristics. For example, it is appreciated that the various elements and features of above described anchor assemblies can be exchanged between the different embodiments. Furthermore, expressed alternatives or modifications to one embodiment are also applicable to the other embodiments. The described embodiments are thus to be considered in all respects only as illustrative and not restrictive. The scope of the invention is, therefore, indicated by the appended claims rather than by the foregoing description. All changes, which come within the meaning and range of equivalency of the claims, are to be embraced within their scope.

We claim:
1. A tissue anchor, comprising:
a body having a longitudinal axis, a proximal end, a distal end, and a longitudinal suture passageway that defines a first suture exit near the distal end and a second suture exit near the proximal end, and comprising a bridge that extends between the first suture exit and the second suture exit, the bridge having a center point defined as the point midway between the first suture exit and the second suture exit, the body being divided into a first portion distal of the center point and a second portion proximal of the center point, wherein the length of the first portion and the length of the second portion are not equal, and the projected surface area of the first portion is substantially equal to the projected surface area of the second portion.

2. The tissue anchor of claim 1, wherein the distal end comprises a distal tapered portion having a sharpened tip.

3. The tissue anchor of claim 2, wherein part of the sharpened tip of the distal tapered portion is removed to provide a bi-angled sharpened tip.

4. The tissue anchor of claim 1, wherein the first portion comprises a slot extending from the distal end to the first suture exit.

5. The tissue anchor of claim 1, wherein the second portion comprises a proximal bore formed at the proximal end of the body and communicating with the suture passageway.

6. The tissue anchor of claim 5, wherein the proximal bore is substantially aligned with the suture passageway.

7. The tissue anchor of claim 5, wherein the proximal bore is not aligned with the suture passageway.

8. The tissue anchor of claim 5, wherein the proximal bore is configured to be geometrically symmetrical relative to a central axis, and the distal end comprises a distal tapered portion having a sharpened tip; and the sharpened tip is substantially in line with the center axis.

9. The tissue anchor of claim 5, further comprising an elongate anchor driver having a distal end configured to releasably fit into the proximal bore.

10. The tissue anchor of claim 9, wherein the second portion of the body and the elongate anchor driver are configured such that, when the distal end of the anchor driver is engaged with the proximal bore of the anchor body, a suture relief feature is provided to allow the suture to reside in the suture relief feature without being pinched by the anchor body and the anchor driver.

11. The tissue anchor of claim 10, wherein the anchor driver has a recess formed in the distal end of the anchor driver, which provides the suture relief feature in cooperation with the proximal bore of the anchor body.

12. A tissue anchor device, comprising:
an elongated body extending along a longitudinal axis, the body comprising:
a distal end and a proximal end, the distal end comprising a tapered portion having a tissue penetrating tip,
a distal channel extending at least through a portion of the tapered portion, the distal channel defining a first suture exit approximate the distal end,
a proximal bore that communicates with the channel, the proximal bore defining a second suture exit approximate the proximal end,
a bridge extending between the first suture exit and the second suture exit, the bridge having a center point defined as the point midway between the first suture exit and the second suture exit, the body being divided into a first portion distal of the center point and a second portion proximal of the center point, wherein the length of the first portion and the length of the second portion are unequal and the projected surface area of the first portion and the projected surface area of the second portion are substantially equal; and an elongate anchor driver having a distal end configured to releasably engage the proximal bore; and a suture configured to pass through the channel and the bore.

13. A tissue anchor device, comprising:

an elongated body extending along a longitudinal axis, the body comprising a projected surface area having a centroid and a centroid plane that is perpendicular to the longitudinal axis and intersects the centroid, the centroid plane dividing the body into a first portion and a second portion, the first portion comprising a first projected surface area and a first dimension, the second portion comprising a second projected surface area and a second dimension, the first projected surface area and the second projected surface area being substantially equal and the first dimension and the second dimension being substantially unequal;

the first portion comprising a tapered portion having a sharpened tip and a channel extending at least through a portion of the tapered portion, the second portion comprising a substantially cylindrical configuration and a bore communicating with the channel;

an elongate anchor driver having an end configured to releasably engage the bore; and a suture configured to pass through the channel and the bore.

14. A tissue anchor device, comprising a body having a projected surface area having a centroid, the body having a longitudinal axis and a centroid plane that is perpendicular to the longitudinal axis and intersects the centroid, the centroid plane dividing the body into a first portion and a second portion, the first portion having a first projected surface area and a first dimension, the second portion having a second projected surface area and a second dimension, the first projected surface area and the second projected surface area being substantially equal and the first dimension and the second dimension being substantially unequal.

15. The tissue anchor of claim 14, wherein the first dimension is one of a first length and a first maximum width and the second dimension is one of a second length and a second maximum width.

* * * * *